(12) United States Patent
Waldmann et al.

(10) Patent No.: US 7,994,289 B2
(45) Date of Patent: Aug. 9, 2011

(54) HUMANIZED ANTI-CD3 ANTIBODIES

(75) Inventors: Herman Waldmann, Oxford (GB); Mark Frewin, Oxford (GB)

(73) Assignee: BTG International Limited, London (GB)

( * ) Notice: Subject to any disclaimer, the term of this patent is extended or adjusted under 35 U.S.C. 154(b) by 399 days.

(21) Appl. No.: 10/463,442

(22) Filed: Jun. 18, 2003

(65) Prior Publication Data

US 2004/0006216 A1    Jan. 8, 2004

Related U.S. Application Data

(63) Continuation of application No. 09/736,371, filed on Dec. 15, 2000, now abandoned, which is a continuation of application No. PCT/GB99/02380, filed on Jul. 21, 1999.

(30) Foreign Application Priority Data

Jul. 21, 1998 (GB) .................................. 9815909.8

(51) Int. Cl.
| | |
|---|---|
| *C07K 16/00* | (2006.01) |
| *C12P 21/08* | (2006.01) |
| *A61K 39/395* | (2006.01) |
| *C12P 21/04* | (2006.01) |

(52) U.S. Cl. ............... 530/387.3; 530/387.1; 530/388.1; 530/388.75; 424/130.1; 424/133.1; 424/141.1; 424/154.1; 435/69.6; 435/70.21

(58) Field of Classification Search ............... 424/133.1, 424/154.1; 530/387.1, 388.2, 387.3, 388.75
See application file for complete search history.

(56) References Cited

U.S. PATENT DOCUMENTS

| | | | |
|---|---|---|---|
| 5,565,332 A | 10/1996 | Hoogenboom et al. | |
| 5,585,097 A * | 12/1996 | Bolt et al. ................. | 424/133.1 |
| 5,693,762 A * | 12/1997 | Queen et al. ............... | 530/387.3 |
| 5,821,337 A | 10/1998 | Carter et al. | |
| 5,968,509 A * | 10/1999 | Gorman et al. ............ | 424/133.1 |
| 6,706,265 B1 * | 3/2004 | Gorman et al. ............ | 424/133.1 |

FOREIGN PATENT DOCUMENTS

WO   WO 93/19196   9/1993

OTHER PUBLICATIONS

Rudikoff et al (Proc. Natl. Acad. Sci. USA 1982 vol. 79 p. 1979).*
Lewin et al. GENES IV, Oxford University Press, p. 810, 1990.*
Paul, Fundamental Immunology, 3rd Edition, 1993, pp. 292-295.*
Fundamental Immunology, William E. Paul, M.D. ed., 3d ed., p. 242, 1993.*
Bolt. S. et al., "The generation of a humanized, non-mitogenic CD3 monoclonal antibody which retains in vitro immunosuppressive properties," Eur. J. Immunol., 23(2):403-411 (1993).
Clark M. et al., "Advantages of rat monoclonal antibodies," Immunol. Today, 4:100-101 (1983).
Clark M.R. & H. Waldmann, "T-cell killing of target cells induced by hybrid antibodies: comparison of two bispecific monoclonal antibodies," J. Natl. Cancer Inst. 79:393-1401 (1987).
Cockett M.I. et al., "High level expression of tissue inhibitor of metalloproteinases in chinese hamster ovary cells using glutamine synthetase gene amplification," Bio/technology, 8:662-667 (1990).
Friend P.J. et al., "Phase I study of an engineered aglycosylated humanised CD3 antibody in renal transplant rejection," Transplantation, 68(11):1632-37 (1999).
Isaacs J.D. et al., "Therapy with monoclonal antibodies. An in vivo model for the assessment of therapeutic potential," J. Immunol., 148:3062-71 (1992).
Page M.J. & M.A. Sydenham, "High level expression of the humanized monoclonal antibody Campath-1H in Chinese hamster ovary cells," Biotechnology, 9:64-68 (1991).
Routledge E.G. et al., "A humanized monovalent CD3 antibody which can activate homologous complement," Eur. J. Immunol., 21(11):2717-25 (1991).
Routledge E.G., et al., "Reshaping antibodies for therapy," In Protein engineering of antibody molecules for prophylactic and therapeutic applications in man (ed. M. Clark) (Academic Titles, Nottingham UK), pp. 13-44 (1993).
Routledge E.G. et al., "The effect of aglycosylation on the immunogenicity of a humanized therapeutic CD3 monoclonal antibody," Transplantation, 60:847-53 (1995).
BioAnaLab Assay Development Report Study No. 09/084-001, Mar. 10, 2010.
Colman, Research in Immunology 145:33-36, 1994.
Rudikoff et al; PNAS 79:1979, 1982.

* cited by examiner

*Primary Examiner* — David J. Blanchard
(74) *Attorney, Agent, or Firm* — Finnegan, Henderson, Farabow, Garrett & Dunner LLP

(57) ABSTRACT

An IgG antibody is provided having a binding affinity for the CD3 antigen complex in which in the heavy chain has a variable region framework together with at least one CDR selected from the amino acid sequences of SEQ ID No 2, 4 and 6 and respective conservatively modified variants thereof and the light chain has a variable region framework together with at least one CDR selected from the amino acid sequences of SEQ ID No 8, 10 and 12 and respective conservatively modified variants thereof characterised in that the heavy chain variable region framework corresponds in sequence to the human type sequence and the light chain variable region framework includes one or more of the specific amino acids characteristic of the rodent type sequence. The novel antibody is capable of being expressed by mammalian cell expression systems at enhanced yields.

14 Claims, 5 Drawing Sheets

Figure 3:
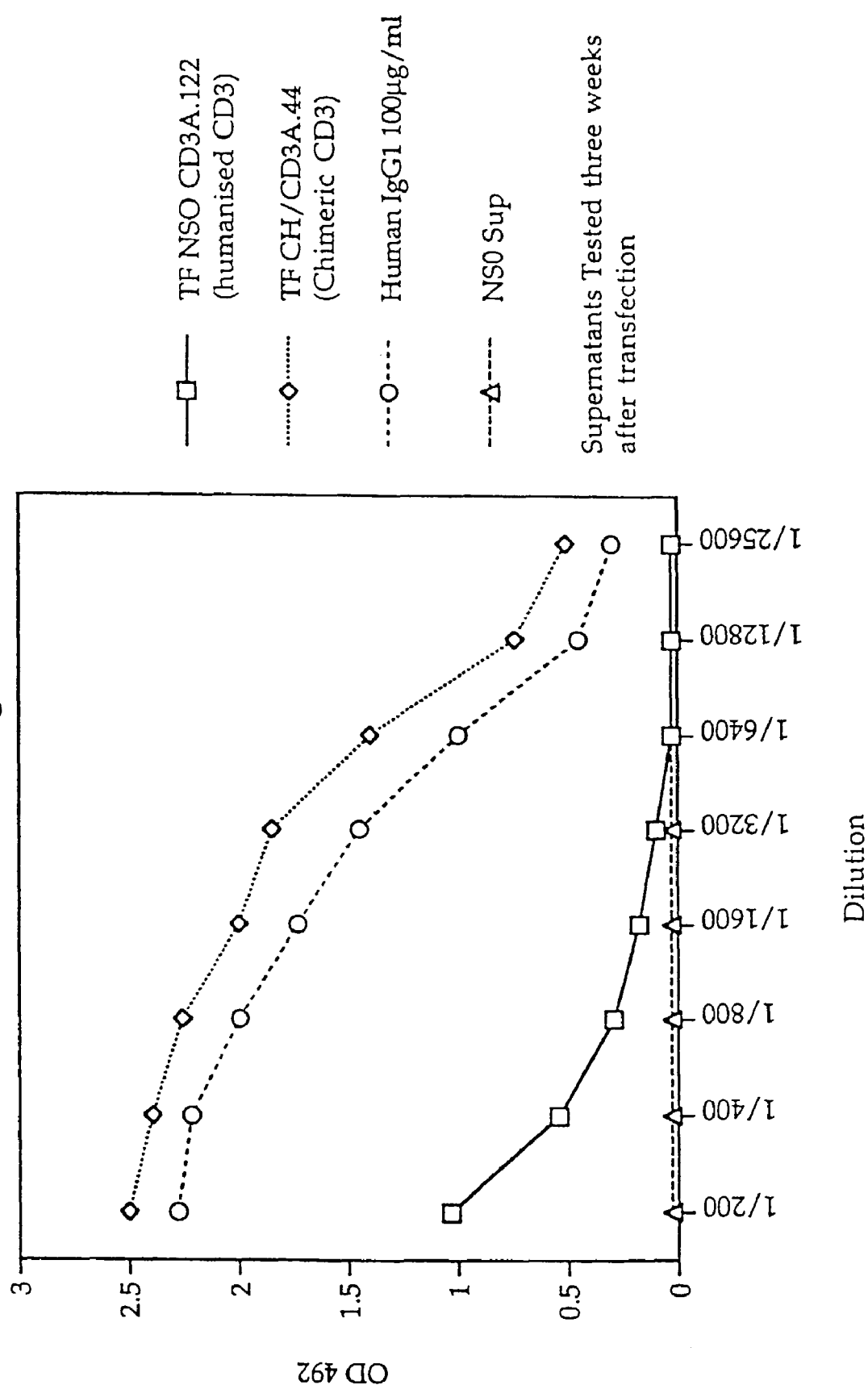

Fig. 1.

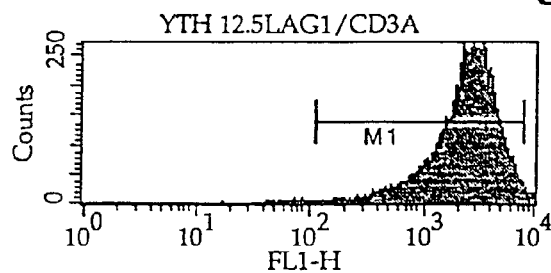

File: YTH 12.5LAG1/CD3A

| Marker | Left, Right | % Gated | Median |
|---|---|---|---|
| All | 1, 9647 | 100.00 | 2458.24 |
| M1 | 111, 7774 | 98.60 | 2458.24 |

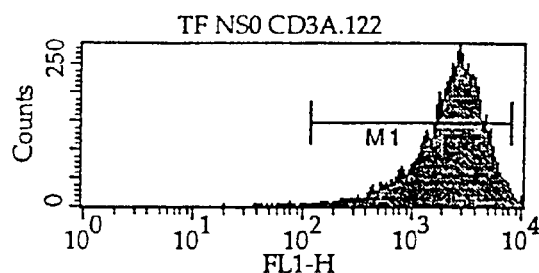

File: TF NS0 CD3A.122

| Marker | Left, Right | % Gated | Median |
|---|---|---|---|
| All | 1, 9647 | 100.00 | 2287.57 |
| M1 | 111, 7774 | 98.78 | 2287.57 |

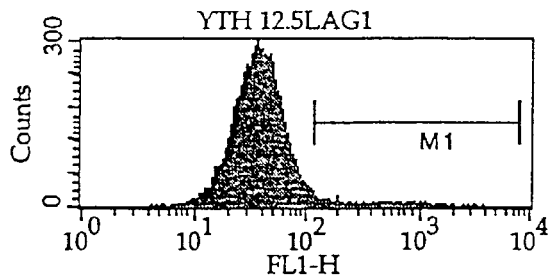

File: YTH 12.5LAG1

| Marker | Left, Right | % Gated | Median |
|---|---|---|---|
| All | 1, 9647 | 100.00 | 37.86 |
| M1 | 111, 7774 | 4.66 | 259.46 |

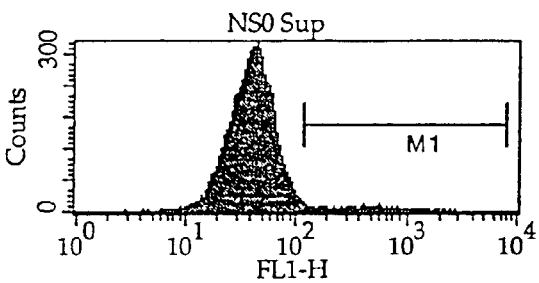

File: NS0 Sup

| Marker | Left, Right | % Gated | Median |
|---|---|---|---|
| All | 1, 9647 | 100.00 | 39.24 |
| M1 | 111, 7774 | 3.68 | 378.55 |

YTH 12.5LAG1/CD3A.27 = rat anti human CD3 light chain + humanised CD3A heavy chain TF NSO CD3A.122 = humanised CD3A YTH 12.5LAg1 = anti human CD3 light chain only NS0 = Transfection line for humanised CD3

Fig.2.
TF 12.5L/CD3A.27
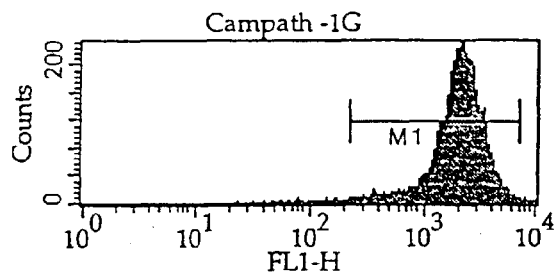
File: Campath -1G
| Marker | Left, Right | % Gated | Median |
|---|---|---|---|
| All | 1, 9647 | 100.00 | 1980.96 |
| M1 | 221, 6978 | 98.56 | 1980.96 |
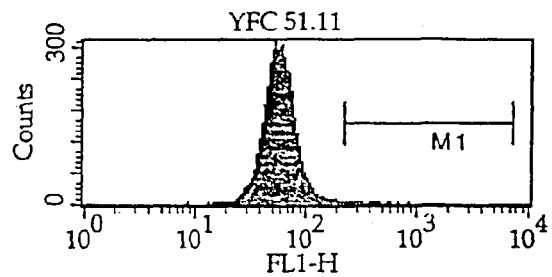
File: YFC 51.11
| Marker | Left, Right | % Gated | Median |
|---|---|---|---|
| All | 1, 9647 | 100.00 | 56.23 |
| M1 | 221, 6978 | 0.56 | 299.61 |
TF 12.5L/CD3A.34
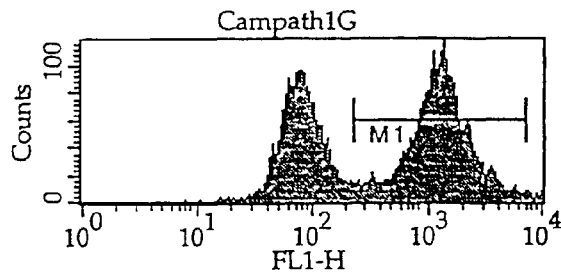
File: Campath1G
| Marker | Left, Right | % Gated | Median |
|---|---|---|---|
| All | 1, 9647 | 100.00 | 673.17 |
| M1 | 221, 6978 | 58.70 | 1197.09 |
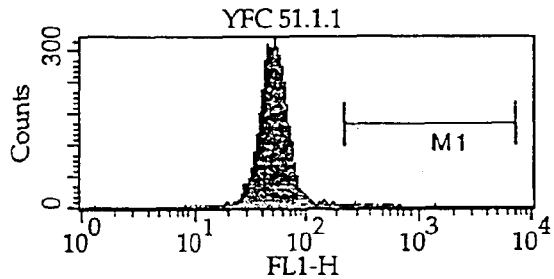
File: YFC 51.1.1
| Marker | Left, Right | % Gated | Median |
|---|---|---|---|
| All | 1, 9647 | 100.00 | 50.48 |
| M1 | 221, 6978 | 0.73 | 339.82 |
Campath-1G = rat anti human CD52 IgG2b
YFC 51.1.1 = rat anti human CD18 IgG2b isotype control TF CH/CD3A.44 = humanised CD3A heavy chain with rat CD3 VL + human Lambda light chain

SEQUENCE LISTING

<160> NUMBER OF SEQ ID NOS: 35

<210> SEQ ID NO 1
<211> LENGTH: 15
<212> TYPE: DNA
<213> ORGANISM: Rattus sp.

<400> SEQUENCE: 1
agctttccaa tggcc                                                    15

<210> SEQ ID NO 2
<211> LENGTH: 5
<212> TYPE: PRT
<213> ORGANISM: Rattus sp.

<400> SEQUENCE: 2

Ser Phe Pro Met Ala
1               5

<210> SEQ ID NO 3
<211> LENGTH: 51
<212> TYPE: DNA
<213> ORGANISM: Rattus sp.

<400> SEQUENCE: 3
accattagta ctagtggtgg tagaacttac tatcgagact ccgtgaaggg c            51

<210> SEQ ID NO 4
<211> LENGTH: 17
<212> TYPE: PRT
<213> ORGANISM: Rattus sp.

<400> SEQUENCE: 4

Thr Ile Ser Thr Ser Gly Gly Arg Thr Tyr Tyr Arg Asp Ser Val Lys
1               5                   10                  15
Gly

<210> SEQ ID NO 5
<211> LENGTH: 30
<212> TYPE: DNA
<213> ORGANISM: Rattus sp.

<400> SEQUENCE: 5
tttcggcagt acagtggtgg ctttgattac                                    30

```
<210> SEQ ID NO 6
<211> LENGTH: 10
<212> TYPE: PRT
<213> ORGANISM: Rattus sp.

<400> SEQUENCE: 6

Phe Arg Gln Tyr Ser Gly Gly Phe Asp Tyr
1               5                   10

<210> SEQ ID NO 7
<211> LENGTH: 39
<212> TYPE: DNA
<213> ORGANISM: Rattus sp.

<400> SEQUENCE: 7
acactcagct ctggtaacat agaaaacaac tatgtgcac                              39

<210> SEQ ID NO 8
<211> LENGTH: 13
<212> TYPE: PRT
<213> ORGANISM: Rattus sp.

<400> SEQUENCE: 8

Thr Leu Ser Ser Gly Asn Ile Glu Asn Asn Tyr Val His
1               5                   10

<210> SEQ ID NO 9
<211> LENGTH: 21
<212> TYPE: DNA
<213> ORGANISM: Rattus sp.

<400> SEQUENCE: 9
gatgatgata agagaccgga t                                                 21

<210> SEQ ID NO 10
<211> LENGTH: 7
<212> TYPE: PRT
<213> ORGANISM: Rattus sp.

<400> SEQUENCE: 10

Asp Asp Asp Lys Arg Pro Asp
1               5

<210> SEQ ID NO 11
<211> LENGTH: 27
<212> TYPE: DNA
<213> ORGANISM: Rattus sp.

<400> SEQUENCE: 11
cattcttatg ttagtagttt taatgtt                                           27

<210> SEQ ID NO 12
<211> LENGTH: 9
<212> TYPE: PRT
<213> ORGANISM: Rattus sp.

<400> SEQUENCE: 12

His Ser Tyr Val Ser Ser Phe Asn Val
1               5

<210> SEQ ID NO 13
<211> LENGTH: 333
<212> TYPE: DNA
<213> ORGANISM: Rattus sp.
```

```
<220> FEATURE:
<221> NAME/KEY: n
<222> LOCATION: (1)..(333)
<223> OTHER INFORMATION: n is a, c, t, g, unknown, or other
<220> FEATURE:
<221> NAME/KEY: misc_feature
<222> LOCATION: (21)..(21)
<223> OTHER INFORMATION: n is a, c, g, or t

<400> SEQUENCE: 13
caggctgttg tgactcaggc naactctgtg tctacgtctc taggaagcac agtcaagctg      60
tcttgcacac tcagctctgg taacatagaa acaactatg tgcactggta ccagctatat     120
gagggaagat ctcccaccac tatgatttat gatgatgata agagaccgga tggtgtccct    180
gacaggttct ctggctccat tgacaggtct ccaactcag ccttcctgac aatcccataat    240 gtggcaattg aagatgaagc tatctacttc tgtcattctt atgttagtag ttttaatgtt    300
ttcggcggtg gaacaaagct cactgtcctt cga                                 333

<210> SEQ ID NO 14
<211> LENGTH: 111
<212> TYPE: PRT
<213> ORGANISM: Rattus sp.

<400> SEQUENCE: 14

Gln Ala Val Val Thr Gln Ala Asn Ser Val Ser Thr Ser Leu Gly Ser
1               5                  10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
        35                  40                  45

Ile Tyr Asp Asp Asp Lys Arg Pro Asp Gly Val Pro Asp Arg Phe Ser
    50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
                85                  90                  95

Ser Phe Asn Val Phe Gly Gly Gly Thr Lys Leu Thr Val Leu Arg
            100                 105                 110

<210> SEQ ID NO 15
<211> LENGTH: 357
<212> TYPE: DNA
<213> ORGANISM: Rattus sp.

<400> SEQUENCE: 15
caggtccaac tgcaggagtc tggggggcggt ttagtgcagc ctggaaggtc catgaaactc       60
tcctgtgcag cctcaggatt cactttcagt agctttccaa tggcctgggt ccgccaggct    120
ccaaagaagg gtctggagtg gtcgcaacc attagtacta gtggtggtag aacttactat     180
cgagactccg tgaagggccg attcactatc tccagagata tgggaaaag catcctatac     240 ctgcaaatga atagtctgag gtctgaggac acggccactt attactgttc aagatttcgg    300
cagtacagtg gtggctttga ttactggggc caagggacca cggtcaccgt ctcctca      357

<210> SEQ ID NO 16
<211> LENGTH: 119
<212> TYPE: PRT
<213> ORGANISM: Rattus sp.

<400> SEQUENCE: 16
```

Gln Val Gln Leu Gln Glu Ser Gly Gly Gly Leu Val Gln Pro Gly Arg
1               5                   10                  15

Ser Met Lys Leu Ser Cys Ala Ala Ser Gly Phe Thr Phe Ser Ser Phe
            20                  25                  30

Pro Met Ala Trp Val Arg Gln Ala Pro Lys Lys Gly Leu Glu Trp Val
        35                  40                  45

Ala Thr Ile Ser Thr Ser Gly Arg Thr Tyr Tyr Arg Asp Ser Val
50                  55                  60

Lys Gly Arg Phe Thr Ile Ser Arg Asp Asn Gly Lys Ser Ile Leu Tyr
65                  70                  75                  80

Leu Gln Met Asn Ser Leu Arg Ser Glu Asp Thr Ala Thr Tyr Tyr Cys
                85                  90                  95

Ser Arg Phe Arg Gln Tyr Ser Gly Gly Phe Asp Tyr Trp Gly Gln Gly
                100                 105                 110

Thr Thr Val Thr Val Ser Ser
            115

<210> SEQ ID NO 17
<211> LENGTH: 648
<212> TYPE: DNA
<213> ORGANISM: Rattus sp.
<220> FEATURE:
<221> NAME/KEY: misc_feature
<222> LOCATION: (21)..(21)
<223> OTHER INFORMATION: n is a, c, g, or t

<400> SEQUENCE: 17
caggctgttg tgactcaggc naactctgtg tctacgtctc taggaagcac agtcaagctg      60
tcttgcacac tcagctctgg taacatagaa acaactatg tgcactggta ccagctatat     120
gagggaagat ctcccaccac tatgatttat gatgatgata agagaccgga tggtgtccct    180
gacaggttct ctggctccat tgacaggtct ccaactcag ccttcctgac aatcccataat    240
gtggcaattg aagatgaagc tatctacttc tgtcattctt atgttagtag ttttaatgtt    300
ttcggcggtg gaacaaagct cactgtcctt cgacagccca aggctgcccc ctcggtcact    360
ctgttcccgc cctcctctga ggagcttcaa gccaacaagg ccacactggt gtgtctcata    420
agtgacttct acccgggagc cgtgacagtg gcctggaaag cagatagcag ccccgtcaag    480
gcgggagtgg agaccaccac accctccaaa caaagcaaca acaagtacgc ggccagcagc    540
tacctgagcc tgacgcctga gcagtggaag tcccacagaa gctacagttg ccaggtcacg    600
catgaaggga gcaccgtgga agagacagtg gcccctacag aatgttca                 648

<210> SEQ ID NO 18
<211> LENGTH: 216
<212> TYPE: PRT
<213> ORGANISM: Rattus sp.

<400> SEQUENCE: 18

Gln Ala Val Val Thr Gln Ala Asn Ser Val Ser Thr Ser Leu Gly Ser
1               5                   10                  15

Thr Val Lys Leu Ser Cys Thr Leu Ser Ser Gly Asn Ile Glu Asn Asn
            20                  25                  30

Tyr Val His Trp Tyr Gln Leu Tyr Glu Gly Arg Ser Pro Thr Thr Met
            35                  40                  45

Ile Tyr Asp Asp Asp Lys Arg Pro Asp Gly Val Pro Asp Arg Phe Ser
        50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
             85                  90                  95

Ser Phe Asn Val Phe Gly Gly Thr Lys Leu Thr Val Leu Arg Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 19
<211> LENGTH: 1347
<212> TYPE: DNA
<213> ORGANISM: Homo sapiens

<400> SEQUENCE: 19
gaggtccaac tgctggagtc tgggggcggt ttagtgcagc ctggagggtc cctgagactc      60
tcctgtgcag cctcaggatt cactttcagt agctttccaa tggcctgggt ccgccaggct     120
ccagggaagg gtctggagtg ggtctcaacc attagtacta gtggtggtag aacttactat     180
cgagactccg tgaagggccg attcactatc tccagagata tagcaaaaa tacctatac      240
ctgcaaatga atagtctgag ggctgaggac acggccgtct attactgtgc aaaatttcgg     300
cagtacagtg gtggctttga ttactggggc caagggaccc tggtcaccgt ctcctcagcc     360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacgccagc     900
acgtaccggg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc cccatcccg ggatgagctg     1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                          1347

<210> SEQ ID NO 20
<211> LENGTH: 449
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Pro Met Ala Trp Val Arg Gln Ala Pro Gly Lys Gly Leu Glu Trp Val
        35                  40                  45

Ser Thr Ile Ser Thr Ser Gly Gly Arg Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu

```
                    370                 375                 380
Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 21
<211> LENGTH: 30
<212> TYPE: PRT
<213> ORGANISM: Homo sapiens

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 22
<211> LENGTH: 14
<212> TYPE: PRT
<213> ORGANISM: Homo sapiens

<400> SEQUENCE: 22

Trp Val Arg Gln Ala Pro Gly Lys Gly Leu Glu Trp Val Ser
1               5                   10

<210> SEQ ID NO 23
<211> LENGTH: 32
<212> TYPE: PRT
<213> ORGANISM: Homo sapiens

<400> SEQUENCE: 23

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 24
<211> LENGTH: 11
<212> TYPE: PRT
<213> ORGANISM: Homo sapiens

<400> SEQUENCE: 24

Trp Gly Gln Gly Thr Leu Val Thr Val Ser Ser
1               5                   10

<210> SEQ ID NO 25
<211> LENGTH: 22
<212> TYPE: PRT
<213> ORGANISM: Rattus sp.

<400> SEQUENCE: 25

Gln Ala Val Val Thr Gln Ala Asn Ser Val Ser Thr Ser Leu Gly Ser
1               5                   10                  15

Thr Val Lys Leu Ser Cys
            20
```

```
<210> SEQ ID NO 26
<211> LENGTH: 15
<212> TYPE: PRT
<213> ORGANISM: Rattus sp.

<400> SEQUENCE: 26

Trp Tyr Gln Leu Tyr Glu Gly Arg Ser Pro Thr Thr Met Ile Tyr
1               5                   10                  15

<210> SEQ ID NO 27
<211> LENGTH: 34
<212> TYPE: PRT
<213> ORGANISM: Rattus sp.

<400> SEQUENCE: 27

Gly Val Pro Asp Arg Phe Ser Gly Ser Ile Asp Arg Ser Ser Asn Ser
1               5                   10                  15

Ala Phe Leu Thr Ile His Asn Val Ala Ile Glu Asp Glu Ala Ile Tyr
            20                  25                  30

Phe Cys

<210> SEQ ID NO 28
<211> LENGTH: 11
<212> TYPE: PRT
<213> ORGANISM: Rattus sp.

<400> SEQUENCE: 28

Phe Gly Gly Gly Thr Lys Leu Thr Val Leu Arg
1               5                   10

<210> SEQ ID NO 29
<211> LENGTH: 36
<212> TYPE: DNA
<213> ORGANISM: Artificial Sequence
<220> FEATURE:
<223> OTHER INFORMATION: Synthetic primer

<400> SEQUENCE: 29
gactacaagc ttacacagga cctcaccatg cgatgg                            36

<210> SEQ ID NO 30
<211> LENGTH: 36
<212> TYPE: DNA
<213> ORGANISM: Artificial Sequence
<220> FEATURE:
<223> OTHER INFORMATION: Synthetic primer

<400> SEQUENCE: 30
gatgctgaat tctgcagctc tagtctcccg tggtgg                            36

<210> SEQ ID NO 31
<211> LENGTH: 34
<212> TYPE: DNA
<213> ORGANISM: Artificial Sequence
<220> FEATURE:
<223> OTHER INFORMATION: Synthetic primer

<400> SEQUENCE: 31
tgaggagacg gtgaccgtgg tcccttggcc ccag                              34

<210> SEQ ID NO 32
<211> LENGTH: 22
<212> TYPE: DNA
<213> ORGANISM: Artificial Sequence
<220> FEATURE:
```

```
<223> OTHER INFORMATION: Synthetic primer
<220> FEATURE:
<221> NAME/KEY: SMRW
<222> LOCATION: (1)..(22)
<223> OTHER INFORMATION: S is C or G, M is A or C, R is A or G,
      W is A or T

<400> SEQUENCE: 32
aggtsmarct gcagsagtcw gg                                              22

<210> SEQ ID NO 33
<211> LENGTH: 21
<212> TYPE: DNA
<213> ORGANISM: Artificial Sequence
<220> FEATURE:
<223> OTHER INFORMATION: Synthetic primer

<400> SEQUENCE: 33
cccaggctgt tgtgactcag g                                               21

<210> SEQ ID NO 34
<211> LENGTH: 21
<212> TYPE: DNA
<213> ORGANISM: Artificial Sequence
<220> FEATURE:
<223> OTHER INFORMATION: Synthetic primer

<400> SEQUENCE: 34
ggaagttgac tcctcgaggt c                                               21

<210> SEQ ID NO 35
<211> LENGTH: 22
<212> TYPE: PRT
<213> ORGANISM: Artificial Sequence
<220> FEATURE:
<223> OTHER INFORMATION: Synthetic Construct

<400> SEQUENCE: 35

Asp Ile Gln Leu Thr Gln Ala Asn Ser Val Ser Thr Ser Leu Gly Ser
1               5                   10                  15

Thr Val Lys Leu Ser Cys
            20
```

HUMANIZED ANTI-CD3 ANTIBODIES

This application is a continuation of application Ser. No. 09/736,371, filed Dec. 15, 2000, now abandoned, the entire content of which is hereby incorporated by reference in this application, which is a continuation of PCT/GB99/02380, filed Jul. 21, 1999, which claims priority under 35 U.S.C. 119/365 to UK Application No. 9815909.8, filed Jul. 21, 1998.

The present invention relates to novel antibodies directed against the CD3 antigen complex, to DNA and RNA encoding for production these antibodies, to cell lines containing such DNA and/or RNA capable of producing them and to methods of producing the antibodies using the DNA, RNA and/or cells.

The human CD3 antigen consists of a minimum of four invariant polypeptide chains, which are non-covalently associated with the T-cell receptors on the surface of T-cells, and is generally now referred to as the CD3 antigen complex. This is intimately involved in the process of T-cell activation in response to antigen recognition by the T-cell receptors. All CD3 monoclonal antibodies can be used to sensitise T-cells to secondary proliferative stimuli such as IL1 (interleukin 1) and IL2 (interleukin 2). In addition, certain CD3 monoclonal antibodies are themselves mitogenic for T-cells. This property is isotype dependent and results from the interaction of the CD3 antibody Fc domain with Fc receptors on the surface of accessory cells.

Rodent CD3 antibodies have been used to influence immunological status by suppressing, enhancing or re-directing T-cell responses to antigens. They therefore have considerable therapeutic potential in the human for use as immunosuppressive agents, for example for the treatment of rejection episodes following the transplantation of renal, hepatic and cardiac allografts.

WO 92/06193 and its equivalents (GB 2249310A, Appn No.s EP. 91917169.4, JP 516117/91 and U.S. Ser. No. 07/862, 543; the contents of which are herein incorporated by reference) address the CD3 antibody antiglobulin response problem by re-shaping or "humanising" the variable region genes for the antibodies and expressing them in association with relevant human constant domain genes. This reduces the non-human content of the monoclonal antibody to such a low level that an antiglobulin response is unlikely.

WO 93/19196 and its equivalents (eg. EP 0586617, U.S. Pat. No. 5,585,097 and U.S. Ser. No. 08/478,684; the contents of which are herein incorporated by reference) address the problem of first dose response. These teach use of aglycosylated humanised CD3 antibodies of the IgG subclass which surprisingly retain their antigen binding specificity and immunosuppressive properties and yet do not induce T cell mitogenesis in vitro and induce a reduced level of cytokine release in vivo, whilst still maintaining some Fc binding ability.

Whilst these CD3 antibodies have great therapeutic value, their production in cell culture has not proven to be easy. In practice poor antibody yield is found accompanied by poor growth of transfected cell line. After much work over several years the best antibody levels achieved have been about 10 μg/ml, with cells expressing CD3 antibodies growing very slowly. Furthermore, these cells go negative over time in hollow cartridge systems used for large scale production.

The Celltech Glutamine Synthesis vector system PEE12 used in the aforesaid expression of CD3 antibodies routinely provides expression of other humanised antibodies at about 200 μg/ml. The original rat hybridoma cell line (YTH 12.5) expressed at a relatively normal level of 100 μg/ml in cell culture, indicating poor antibody production to be associated with the humanised form. It appears that it is one or more of the expressed humanised proteins that proves toxic to the cells, as following transfection of cells they go negative faster than they grow.

The present inventors have now surprisingly found that by producing a chimeric form of the anti-CD3 antibody, linking the rat CD3 light chain variable region with the human lambda constant region and cloning this into PEE12 containing humanised CD3 aglycosyl heavy chain, they can produce myleoma cell lines which provide expression of functional aglycosylated CD3 antibodies at 60 to 100 μg/ml of culture. By use of limiting dilution cloning some of the clones can be selected to provide still higher expression levels, eg. of the order of 120 μg/ml, and remain stable in long term culture with large scale production with no untoward effect on cell growth. Thus the present invention's chimeric antibodies offer good production capability without antiglobulin response normally associated with rat derived antibodies.

Accordingly, the present invention provides an IgG antibody having a binding affinity for the CD3 antigen complex in which in the heavy chain has a variable region framework together with at least one CDR selected from the amino acid sequences of SEQ ID No 2, 4 and 6 and respective conservatively modified variants thereof and the light chain has a variable region framework together with at least one CDR selected from the amino acid sequences of SEQ ID No 8, 10 and 12 and respective conservatively modified variants thereof characterised in that the heavy chain variable region framework corresponds in sequence to the human type sequence and the light chain variable region includes one or more of the specific amino acids characteristic of the rodent type sequence.

Preferably the light chain variable region includes sufficient amino acids specific to the rodent type sequence such that the light and heavy chains associate more strongly than when the light chain variable region is of the corresponding fully human type. This can conveniently be such that the light chain variable region corresponds entirely to the rodent, eg. rat, sequence. Alternatively, only some or even one of the rat characteristic amino acids may be included.

Particular amino acids that are of rodent type rather than human type in the light chain variable region sequence are selected from those shown in SEQ ID No 14 in the sequence listing attached hereto, that being a preferred light chain variable region framework sequence wherein all the possible rat framework characteristic amino acids have been included, together with the respective CDR sequences. Thus amino acids characteristic of rat light chain variable framework region in SEQ ID No 14 are: Gln-1, Ala-2, Val-3, Val-4, Ala-7, Asn-8, Thr-12, Leu-14, Ser-16, Lys-19, Leu-20, Leu-39, Tyr-40, Glu-41, Ser-44, Met-48, Tyr-50, Phe-75, His-79, Asn-80, Val-81, Ala-82, Ile-83, Ile-88 and Phe-90. The corresponding human amino acids are in each case Asp-1, Phe-2, Met-3, Leu-4, Pro-7, His-8, Glu-12, Pro-14, Lys-16, Ile-19, Ile-20, Gln-39, Arg-40, Pro-41, Ala-44, Val-48, Phe-50, Ser-75, Ser-79, Gly-80, Leu-81, Gln-82, Thr-83, Asp-88 and Tyr-90. The latter human sequence is illustrated in EP 0586617 B on page 6 and in the corresponding U.S. patent application Conveniently the heavy chain variable region framework is of human type and the light chain variable region is of rodent type, that being with all the aforespecified amino acids being the rat type of SEQ ID No 14. However, one or more, but not all of these positions of SEQ ID No 14 may be of the human type as long as sufficient rodent, eg. rat, sequence is present to enable stable light-heavy chain interaction to be achieved over that provided by the fully humanised form of the prior art. Such interaction is preferably such that when the antibody is expressed in PEE12 cells using suppliers (Celltech) instructions in excess of 50 µg/ml is achieved, more preferably in excess of 100 µg/ml. Preferably such cells should not go negative in significant numbers after several weeks use.

It will be realised by those skilled in the art that techniques such as site directed mutagenesis using PCR will allow the necessary production of these various light variable chains such that all embodiments of the invention may be produced without undue burden and screened for expression levels from the PEE12 cells.

The CDR amino sequences of SEQ ID No 2, 4, 6, 8, 10 and 12 correspond to CDRs (a), (b), (c), (d), (e) and (f) of WO 93/19196 and the CDRs themselves may also be referred to as respective CDRs (a) to (f) below.

Preferably the heavy chain and/or light chain each have all three of their respective CDRs of SEQ ID No 2, 4 and 6 and SEQ. ID. No 8, 10 and 12.

Preferably the antibody is aglycosylated. The term aglycosylated is employed in its normal usage to indicate that the antibodies according to the invention are not glycosylated.

By the term human type with respect to the framework region is meant a framework that is similar enough to human framework that it is substantially-non-immunogenic in human when present in an intact antibody. Preferably an antibody of the invention having a heavy chain with a human type framework has between 60 and 140%, more typically at least 80 to 100%, of the rodent antibody affinity for the CD3 antigen. Characteristics of humanised monoclonal antibodies and methods for producing these from rodent monoclonals are disclosed in U.S. Pat. No. 5,585,089, the content of which is incorporated herein by reference for such purpose. Comparison of the human type heavy chain variable region with that of its rat counterpart can be made by comparing SEQ ID No 16 (rat) with the corresponding region found at the N-terminal of SEQ ID No 20. SEQ ID No 15 is that of DNA encoding for SEQ ID No 16. Thus a human type framework region may have, for example, seven or more of the thirteen changes that distinguish the sequence of the N-terminal 119 amino acids of SEQ ID No 20 from that of SEQ ID No 16. More preferably all the amino acids of the human type are incorporated. These changes may be at, for example, any of positions 5, 18, 19, 42, 49, 75, 77, 78, 88, 93, 97, 98 and 114 of these sequences.

By the term rodent type with respect to the framework region is meant a framework that correspond in amino acid sequence to that of an antibody of a rodent, eg. a rat or a mouse. In the case of anti-CD3 antibodies convenient framework amino acids are those of a rat antibody.

Further discussion of CD3 antigens is to be found in the report of the First International Workshop and Conference on Human Leukocyte Differentiation Antigens and description of various glycosylated antibodies directed against the CD3 antigen is also to be found in the reports of this series of Workshops and Conferences, particularly the Third and Fourth, published by Oxford University Press. Specific examples of such antibodies include those described by Van Lier et al., Euro. J. Immunol., 1987, 17, 1599-1604, Alegre et al., J. Immunol., 1991, 140, 1184, and by Smith et al., ibid, 1986, 16, 478, the last publication relating to the IgG1 antibody UCHT1 and variants thereof.

However, of particular interest as the basis for antibodies according to the present invention are the CDRs contained in the antibodies OKT3 and YTH 12.5.14.2. The antibody OKT3 is discussed in publications such as Chatenaud et al., Transplantation, 1991, 51, 334 and the New England Journal of Medicine paper, 1985, 313, 339, and also in patents EP 0 018 795 and U.S. Pat. No. 4,361,539. The antibody YTH 12.5.14.2 (hereinafter referred to as YTH 12.5) is discussed in publications such as Clark et al., European J. Immunol., 1989, 19, 381-388 and reshaped YTH 12.5 antibodies are the subject of EP 0504350 and its equivalents U.S. Ser. No. 08/362,780 and U.S. Pat. No. 5,585,097, these applications describing in detail the CDRs present in this antibody. The contents of U.S. Ser. No. 08/362,780, U.S. Pat. No. 5,585,097 and U.S. Pat. No. 4,361,539 are incorporated herein by reference The term "conservatively modified variants" is one well known in the art and indicates variants containing changes which are substantially without effect on antibody-antigen affinity. This term is conveniently defined as found in U.S. Pat. No. 5,380,712 which is incorporated herein by reference for such purpose.

Of the CDRs it is the heavy chain CDRs (a), (b) and (c) are of most importance. It will be realised by those skilled in the art that the antibodies of the invention also comprise constant domains.

The CDRs (a), (b) and (c) are arranged in the heavy chain in the sequence in the order: human framework region 1/(a)/human framework region 2/(b)/human framework region 3/(c)/human framework region 4 in a leader to constant domain (n-terminal to C-terminal) direction and the CDRs (d), (e) and (f) are arranged in the light chain in the sequence: rodent framework region 1/(d)/rodent framework region 2/(e)/rodent framework region 3/(f)/rodent framework region 4 in a leader to constant domain direction. It is preferred, therefore, that where all three are present the heavy chain CDRs are arranged in the sequence (a), (b), (c) in a leader to constant domain direction and the light chain CDRs are arranged in the sequence (d), (e), (f) in a leader to constant domain direction. The rodent framework region is preferably rat.

It should be appreciated however, that antibodies according to the invention may contain quite different CDRs from those described hereinbefore and that, even when this is not the case, it may be possible to have heavy chains and particularly light chains containing only one or two of the CDRs (a), (b) and (c) and (d), (e) and (f), respectively. However, although the presence of all six CDRs defined above is therefore not necessarily required in an antibody according to the present invention, all six CDRs will most usually be present in the most preferred antibodies.

A particularly preferred antibody therefore has a human type heavy chain with the three CDRs (a), (b) and (c) comprising the amino acid sequences SEQ ID No 2, 4 and 6 or respective conservatively modified variants thereof and a rat light chain with the three CDRs (d), (e) and (f) comprising the amino acid sequences SEQ ID No 8, 10 and 12 or respective conservatively modified variants thereof in which the heavy chain CDRs are arranged in the order (a), (b), (c) in the leader constant region direction and the light chain CDRs are arranged in the order (d), (e), (f) in the leader constant region direction.

A preferred form of the first aspect of the present invention provides an antibody, particularly aglycosylated, which has a binding affinity for the human CD3 antigen in which the antibody constant region is of or is derived from one of human origin, particularly being the lambda constant region attached to the rat light chain variable region.

One convenient possibility is for the antibody to have a rat light chain variable domain framework region corresponding in amino acid sequence to that in the YTH12.5 hybridoma, ie. that of SEQ ID No 14, although the constant region will still preferably be of or derived from one of those of human origin, eg. will be the human lambda constant region. A preferred rat human chimeric light chain and lambda constant region amino acid sequence is that of SEQ ID No 18. Recombinant nucleic acid, eg. DNA, encoding for YTH12.5 comprises an amino acid sequence of SEQ ID No 13 while that encoding the rat light chain variable region and the human lambda constant region comprises SEQ ID No 17.

Certain human heavy chain variable domain framework sequences will be preferable for the grafting of the preferred CDR sequences, since the 3-dimensional conformation of the CDRs will be better maintained in such sequences and the antibody will retain a high level of binding affinity for the antigen. The heavy chain variable (V) region frameworks are preferably those coded for by the human VH type III gene VH26.D.J. which is from the B cell hybridoma cell line 18/2 (Huminghat, Dersimonian et al., Journal of Immunology, 139, 2496-2501; WO 93/19196 and U.S. Ser. No. 08/478, 684)).

In a preferred form of the first aspect of the present invention the one or more preferred CDRs of the heavy chain of the rat anti-CD3 antibody are therefore present in a human variable domain framework which has the following amino acid sequence reading in the leader to constant region direction, CDR indicating a CDR (a), (b) or (c) as defined hereinbefore, a conservatively modified variant thereof or an alternative CDR:—

SEQ ID No 21/CDR/SEQ ID No 22/CDR/SEQ ID No 23/CDR/SEQ ID No 24

Similarly, the one or more preferred CDRs of the light chain of the rat CD3 antibody are present in a rodent variable domain framework which has the following amino acid sequence reading in the leader to constant region direction, CDR indicating a CDR (d), (e) and (f) as defined hereinbefore, a conservatively modified variant thereof or an alternative CDR:—

SEQ ID No. 25/CDR/SEQ ID No. 26/CDR/SEQ ID No. 27/CDR/SEQ ID No. 28.

In an aglycosylated antibody containing all three preferred light chain CDRs the light chain variable region comprises SEQ ID No 14:—

The heavy and light chain constant regions can be based on antibodies of different types as desired subject to the antibody being an IgG antibody, but although they may be of or derived from those of rodent, eg. rat or mouse, origin they are preferably of or are derived from those of human origin. As described above, for the light chain the constant region is preferably of the lambda type and for the heavy chain it is preferably of an IgG isotype, especially IgG1, modified to effect aglycosylation as appropriate.

In an aglycosylated antibody containing all three preferred heavy chain CDRs, the heavy chain variable region and human IgG1 CH1-hinge aglycosylCH2CH3 comprises SEQ ID No 20 and is encoded for by DNA of SEQ ID No 19.

All human constant regions of the IgG isotype are known to be glycosylated at the asparagine residue at position 297, which makes up part of the N-glycosylation motif Asparagine$^{297}$-X$^{298}$-Serine$^{299}$ or Threonine$^{299}$, where X is the residue of any amino acid except proline. The antibody of the invention may thus be aglycosylated by the replacement of Asparagine$^{297}$ in such a constant region with another amino acid which cannot be glycosylated. Any other amino acid residue can potentially be used, but alanine is the most preferred. Alternatively, glycosylation at Asparagine$^{297}$ can be prevented by altering one of the other residues of the motif, e.g. by replacing residue 298 by proline, or residue 299 by any amino acid other than serine or threonine. Techniques for performing this site directed mutagenesis are well known to those skilled in the art and may for example be performed using a site directed mutagenesis kit such, for example, as that commercially available from Amersham. The procedure is further exemplified hereinafter.

It is well recognised in the art that the replacement of one amino acid in a CDR with another amino acid having similar properties, for example the replacement of a glutamic acid residue with an aspartic acid residue, may not substantially alter the properties or structure of the peptide or protein in which the substitution or substitutions were made. Thus, the aglycosylated antibodies of the present invention include those antibodies containing the preferred CDRs but with a specified amino acid sequence in which such a substitution or substitutions have occurred without substantially altering the binding affinity and specificity of the CDRs. Alternatively, deletions may be made in the amino acid residue sequence of the CDRs or the sequences may be extended at one or both of the N- and C-termini whilst still retaining activity.

Preferred aglycosylated antibodies according to the present invention are such that the affinity constant for the antigen is $10^5$ moles$^{-1}$ or more, for example up to $10^{12}$ mole$^{-1}$. Ligands of different affinities may be suitable for different uses so that, for example, an affinity of $10^6$, $10^7$ or $10^8$ mole$^{-1}$ or more may be appropriate in some cases. However antibodies with an affinity in the range of $10^6$ to $10^8$ mole$^{-1}$ will often be suitable. Conveniently the antibodies also do not exhibit any substantial binding affinity for other antigens. Binding affinities of the antibody and antibody specificity may be tested by assay procedures such as those described in the Examples section of EP 0586617 and U.S. Ser. No. 08/478,684 and U.S. Pat. No. 5,585, 097, incorporated herein by reference, (See Example 5—Effector Cell Retargetting Assay), or by techniques such as ELISA and other immunoassays.

Antibodies according to the invention are aglycosylated IgG CD3 antibodies having a "Y" shaped configuration which may have two identical light and two identical heavy chains and are thus bivalent with each antigen binding site having an affinity for the CD3 antigen. Alternatively, the invention is also applicable to antibodies in which only one of the arms of the antibody has a binding affinity for the CD3 antigen. Such antibodies may take various forms. Thus the other arm of the antibody may have a binding affinity for an antigen other than CD3 so that the antibody is a bispecific antibody, for example as described in U.S. Pat. No. 4,474,893 (incorporated herein by reference) and European Patent Applications Nos. 87907123.1 and 87907124.9. Alternatively, the antibody may have only one arm which exhibits a binding affinity, such an antibody being termed "monovalent".

Monovalent antibodies (or antibody fragments) may be prepared in a number of ways. Glennie and Stevenson (Nature, 295, 712-713, (1982)) describe a method of preparing monovalent antibodies by enzymic digestion. Stevenson et al. describe a second approach to monovalent antibody preparation in which enzymatically produced Fab' and Fc fragments are chemically cross-linked (Anticancer Drug Design, 3, 219-230 (1989)). In these methods the resulting monovalent antibodies have lost one of their Fab' arms. A third method of preparing monovalent antibodies is described in European Patent No. 131424. In this approach the "Y" shape of the antibody is maintained, but only one of the two Fab' domains will bind to the antigen. This is achieved by introducing into the hybridoma a gene coding for an irrelevant light chain which will combine with the heavy chain of the antibody to produce a mixture of products in which the monovalent antibody is the one of interest.

More preferably, however, the monovalent aglycosylated CD3 antibodies of the invention are prepared by the following method. This involves the introduction into a suitable expression system, for example a cell system as described hereinafter, together with genes coding for the heavy and light chains, of a gene coding for a truncated heavy chain in which the variable region domain and first constant region domain of the heavy chain are absent, the gene lacking the exon for each of these domains. This results in the production by the cell system of a mixture of (a) antibodies which are complete bivalent antibodies, (b) antibody fragments consisting only of two truncated heavy chains (i.e. an Fc fragment) and (c) fragments of antibody which are monovalent for the CD3 antigen, consisting of a truncated heavy chain and a light chain in association with the normal heavy chain. Such an antibody fragment (c) is monovalent since it has any only one Fab' arm. Production of a monovalent antibody in the form of such a fragment by this method is preferred for a number of reasons. Thus, the resulting antibody fragment is easy to purify from a mixture of antibodies produced by the cell system since, for example, it may be separable simply on the basis of its molecular weight. This is not possible in the method of European Patent No. 131424 where the monovalent antibody produced has similar characteristics to a bivalent antibody in its size and outward appearance.

Additionally, the production of a monovalent antibody fragment by the new method uses conditions which can more easily be controlled and is thus not as haphazard as an enzyme digestion/chemical coupling procedure which requires the separation of a complex reaction product, with the additional advantage that the cell line used will continue to produce monovalent antibody fragments, without the need for continuous synthesis procedures as required in the enzyme digestion/chemical coupling procedure.

It is believed that aglycosylated antibodies according to the invention do not occur in nature and these aglycosylated antibodies may in general be produced synthetically in a number of ways. Most conveniently, however, appropriate gene constructs for the constant and variable regions of the heavy and light chains which are present in the antibody are separately obtained and then inserted in a suitable expression system.

Genes encoding the variable domains of a ligand of the desired structure may be produced and conveniently attached to genes encoding the constant domains of an antibody which have undergone site directed mutagenesis. These constant genes may be obtained from hybridoma cDNA or from the chromosomal DNA and have undergone site directed mutagenesis to produce the aglycosylated constant regions. Genes encoding the variable regions may also be derived by gene synthesis techniques used in the identification of the CDRs contained herein. Suitable cloning vehicles for the DNA may be of various types.

It will be realised by those skilled in the art that such genes may provided by a variety of methods. For example, it is possible to (i) raise a series of hybridomas against the CD3 antigen in the known manner,g (ii) prepare DNA from these hybridomas by the procedures set out in WO 92/06193 and WO 93/19196 and their corresponding U.S. patents by extracting mRNA and converting this to cDNA using PCR, (iii) screen this cDNA with oligonucleotide probes corresponding in sequence to CDR complementary DNA sequences, (iv) sequencing any positively identified hybridoma and (v) re-shaping the rat sequence by humanizing techniques set out in the aforesaid patents. In order to enable production of several and preferably all six preferred CDRs, site directed mutagenesis may be employed to insert desired DNA at corresponding points in the framework encoding DNA.

Expression of these genes through culture of a cell system to produce a functional CD3 ligand is most conveniently effected by transforming a suitable prokaryotic or particularly eukaryotic cell system, particularly an immortalised mammalian cell line such as a myeloma cell line, for example the YB2/3.01/Ag20 (hereinafter referred to as YO) rat myeloma cell, NS0 myeloma cell, or Chinese hamster ovary cells (although the use of plant cells is also of interest), with expression vectors which include DNA coding for the various antibody regions, and then culturing the transformed cell system to produce the desired antibody. Such general techniques of use for the manufacture of ligands according to the present invention are well known in the art and are described in publications such as "Molecular Cloning" by Sambrook, Fritsch and Maniatis, Cold Spring Harbour Laboratory Press, 1989 (2nd edition). The techniques are further illustrated by the Examples contained in WO 93/19196 and U.S. Ser. No. 08/478,684, incorporated herein by reference.

A second aspect of the present invention thus provides a process for the preparation of an aglycosylated IgG antibody according to the first aspect having a binding affinity for the CD3 antigen which comprises culturing cells capable of expressing the antibody in order to effect expression thereof. A third aspect of the invention also provides a cell line which expresses an aglycosylated antibody according to the invention per se.

Preferred among such cell lines are those which comprise DNA sequences encoding the preferred CDRs described hereinbefore. A group of nucleotide sequences coding for the CDRs (a) to (f) described hereinbefore is as indicated under (a) to (f) below, respectively, but it will be appreciated that the degeneracy of the genetic code permits variations to be made in these sequences whilst still encoding for the CDRs' amino acid sequences.

(a) SEQ ID No 1; (b) SEQ ID No. 3; (c) SEQ ID No. 5; (d) SEQ ID No. 7; (e) SEQID No. 9; (f) SEQ ID No. 11

Such cell lines will particularly contain larger DNA sequences which comprise (1) DNA expressing human heavy chain variable framework regions carrying one or more of (a), (b) and (c), and (2) DNA expressing rodent, eg. rat light chain variable framework regions carrying one or more of (d), (e) and (f).

A specific example of such DNA is SEQ ID No 19 which codes for the CDRs (a), (b) and (c) arranged in the heavy chain framework coded for by the human VH type III gene VH26.D.Jlinked to the human IgG. CH1-hinge-aglycosyl-CH2CH3 as discussed hereinbefore and that sequence SEQ ID No 17 which codes for the CDRs (d), (e) and (f) arranged in the light chain framework coded for by the YTH 12.5 human lambda constant region chimeric protein.

The chimeric partially humanised aglycosylated antibodies in accordance with the present invention have therapeutic value, particularly in immunosuppression, particularly in the control of graft rejection, where it is especially desirable that immunosuppression is temporary rather than total, and thus that T-cells are not completely destroyed, but instead rendered non-functional by antibody blockade of the CD3 antigen-TCR complex. In addition, the aglycosylated CD3 antibodies may have potential in other areas such as in the treatment of cancer, specifically in the construction of bispecific antibodies (for effector cell retargetting) or antibody-toxin conjugates, where the efficacy of the therapeutic agent would be compromised by Fc-mediated killing of the effector cells or non-specific killing of Fc receptor bearing cells respectively.

In a fourth aspect, the present invention thus includes a method of treating patients with cancer, particularly a lymphoma, or for immunosuppression purposes, for instance in a case where graft rejection may occur, comprising administering a therapeutically effective amount of an aglycosylated antibody in accordance with the first aspect of the invention.

Aglycosylated antibodies in accordance with the first aspect of the invention may be formulated for administration to patients by administering the said antibody together with a physiologically acceptable diluent or carrier. The antibodies are preferably administered in an injectable form together with such a diluent or carrier which is sterile and pyrogen free. By way of guidance it may be stated that a suitable dose of antibody is about 1-10 mg injected daily over a time period of, for example 10 days, although due to the elimination of the first dose response it will be possible if desired to adminster higher amounts of the antibody, for example even up to 100 mg daily, depending on the individual patient's needs. Veterinary use is on a similar g/kg dosage basis.

The invention will now be described by way of is illustration only by reference to the following non-limiting Examples, Figures and Sequence listing. Further embodiments of the invention falling within the scope of the claims will occur to those skilled in the art in the light of these.

FIGURES

FIG. 1: shows plots of FACS assay of binding of fully humanised aglycosyl CD3 (of EP0586617, U.S. Ser. No. 08/478,684 and U.S. Pat. No. 5,585,097) and a chimeric antibody of the present invention in which a rat light variable framework region is employed. Light chain YTH12.5LAG1 alone does not show normal binding as this is not associated with a heavy chain FIG. 2: shows plots of FACS assay of binding of two chimeric transfectants produced using pOXD52neo vector and thus which express CD52 antigen on their surfaces. These illustrate use of pOXCD52neo vector as a way of monitoring whether transfectants are a clonal population. TF 12.5L/CD3A..27 has one peak when stained with CD52 showing all cells are producing CD3 antibody, whereas TF12.5L/CD3A.34 has two peaks showing a negative population of cells that do not produce CD3 antibody.

FIG. 3: shows plots of $OD_{492}$ against dilution in an ELISA comparing human IgG production as a measure of antibody yield for present chimeric and prior art humanised aglycosylCD3. CD3 supernatants tested three weeks after transfection show the cell containing DNA encoding for a chimeric antibody of the present invention producing about 120 μg/ml and that the fully humanised CD3 producing less than 10 μg/ml.

Figure 4:
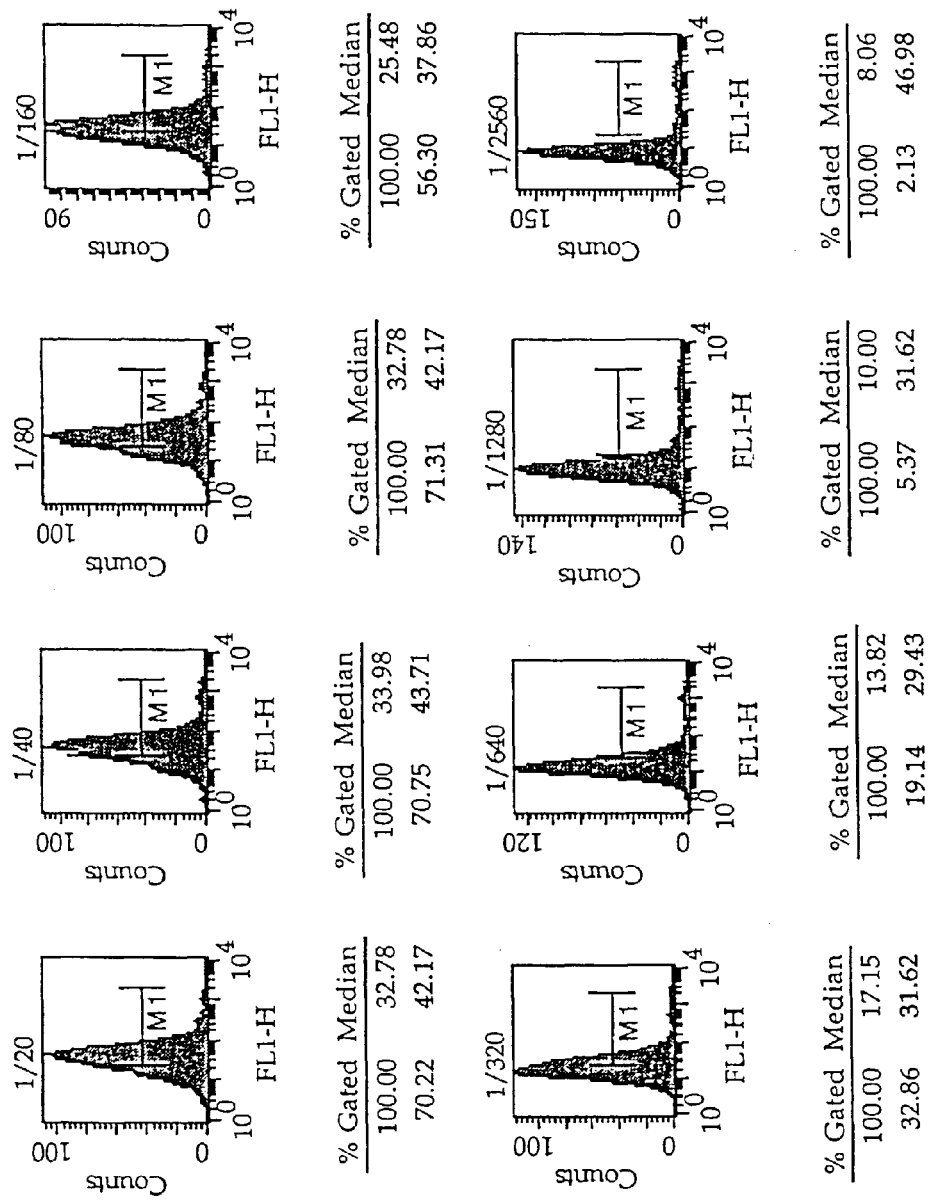
Figure 5:
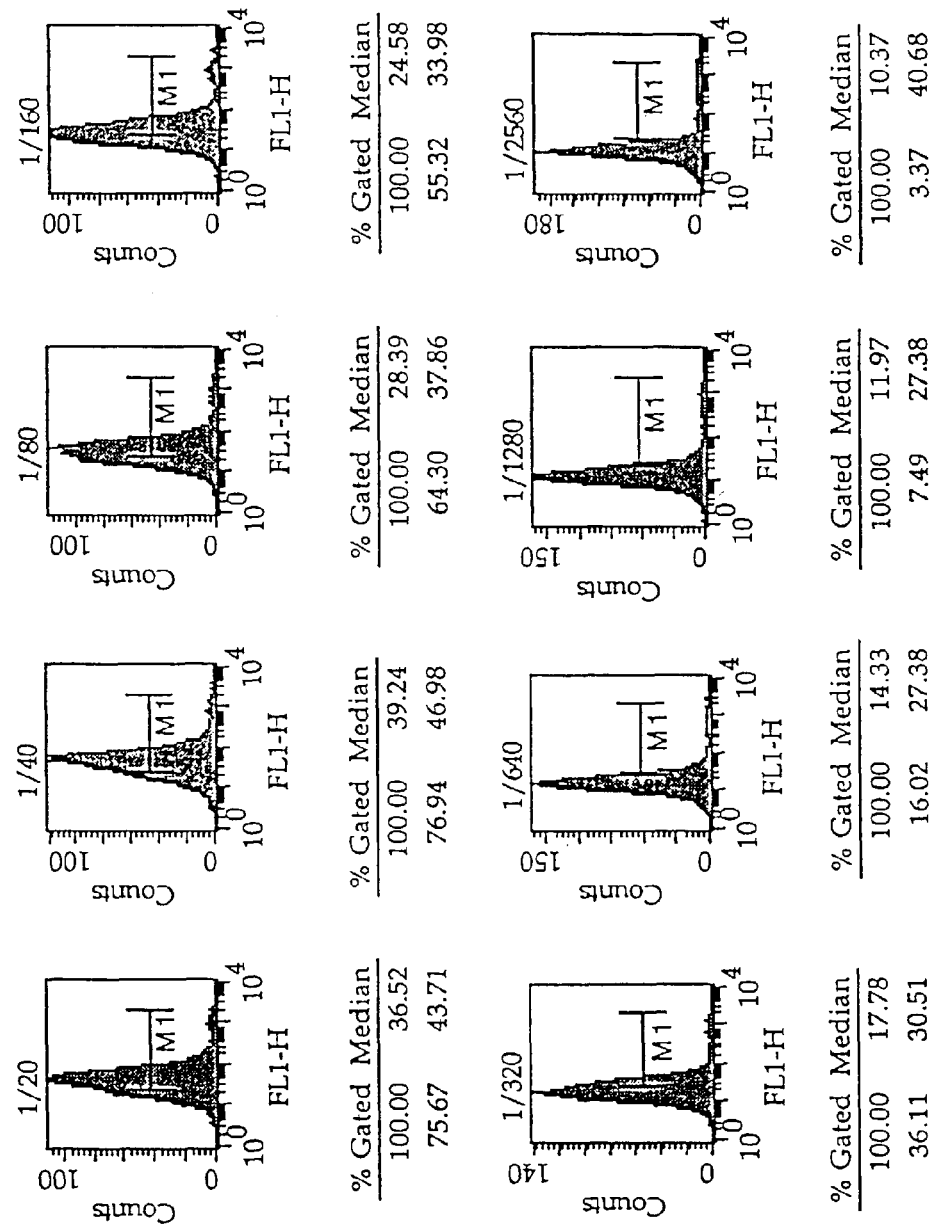

FIGS. 4 and 5: show binding plots of the present invention chimeric antibodies and fully humanised CD3 to Jurkat cells for antibody affinity. Starting from a known concentration of 100 μg/ml and then diluting to 1/20 and seven fold titrations to 1/2560. The staining patterns demonstrate that the affinities are the same.

SEQUENCE LISTING

SEQ ID No 1 is that of DNA encoding for CDR (a).
SEQ ID No 2 is the amino acid sequence of CDR (a).
SEQ ID No 3 is that of DNA encoding for CDR (b).
SEQ ID No 4 is the amino acid sequence of CDR (b).
SEQ ID No 5 is that of DNA encoding for CDR (c).
SEQ ID No 6 is the amino acid sequence of CDR (c).
SEQ ID No 7 is that of DNA encoding for CDR (d).
SEQ ID No 8 is the amino acid sequence of CDR (d).
SEQ ID No 9 is that of DNA encoding for CDR (e).
SEQ ID No 10 is the amino acid sequence of CDR (e).
SEQ ID No 11 is that of DNA encoding for CDR (f).
SEQ ID No 12 is the amino acid sequence of CDR (f).
SEQ ID No 13 is that of DNA encoding for the rat light chain variable region.
SEQ ID No 14 is the amino acid sequence of the rat light chain variable region.
SEQ ID No 15 is that of DNA encoding the rat heavy chain variable region including the respective CDRs.
SEQ ID No 16 is the amino acid sequence of the rat heavy chain variable region including the respective CDRs.
SEQ ID No 17 is that of DNA encoding the rat light chain variable region with respective CDRs and the human lambda constant region.
SEQ ID No 18 is the amino acid sequence of the rat light chain variable region with respective CDRs and the human lambda constant region.
SEQ ID No 19 is the DNA sequence encoding for the heavy chain variable region with CDRs and the human CH1-hinge-aglycosyl$CH_2CH_3$.
SEQ ID No 20 is the amino acid sequence of the heavy chain variable region with CDRs and the human CH1-hinge-aglycosyl$CH_2CH_3$.
SEQ IDs No 21 to 24 are the amino acid sequences of the human heavy chain variable domain framework without CDRs.
SEQ IDs No 25 to 28 are the amino acid sequences of the rat light chain variable domain framework without CDRs.
SEQ ID No 29 and 30 are of primers used to clone rat CD3 light chain variable region into PEE12.

GENERAL METHODOLOGY
General Methods of Producing CD3 Specific Monoclonal Antibodies with Humanised Heavy Chain.

The cloning and re-shaping of the V-region gene of the rat antibody YTH 12.5 specific for the human CD3 antigen is performed as described in Routledge et al., 1991, Eur. J. Immunol., 21, 2717 and in UK Patent Application No. 9121126.8 and its equivalents. YTH 12.5 is a rat hybridoma cell line secreting an IgG2b monoclonal antibody specific for the CD3 antigen complex, but the methodology is applicable to other cells secreting CD3 specific antibodies with the same CDRs (see the preceding description).

Briefly, the methodology is based on that of Orlandi et al., 1989, PNAS USA, 86, 3833, using the polymerase chain reaction (PCR). The $V_H$ coding region (heavy chain variable region coding region) is cloned using oligonucleotide primers VH1FOR (5'-d(TGAGGAGACGGTGACCGTGGTCCCT-TGGCCCCAG)) (SEQ ID NO:31) and VH1BACK (5'-d(AG-GTSMARCTGCAGSAGTCWGG)) (SEQ ID NO:32) (see aforesaid incorporated patents). The PCR products are ligated into the vector M13-VHPCR1 in which site directed mutagenesis is performed using 6 oligonucleotide primers. The $V_L$ coding region (light chain variable region coding region) was cloned using primers designed based on the published $V_L$ sequences. In a preferred embodiment, these primers are the VL-Backward primer (5'-CCCAGGCTGTTGT-GACTCAGG-3') (SEQ ID NO:33) and the VL-Forward primer (3'-GGAAGTTGACTCCTCGAGGTC-5') (SEQ ID NO:34) disclosed in U.S. application Ser. No. 08/362,780, now U.S. Pat. No. 5,968,509. The gene is cloned into the vector M13-VKPCR1, together with the human lambda light chain constant region. In this vector mutagenesis of the $V_L$ framework is performed using 5 oligonucleotides. The humanised V_L gene is then inserted into the expression vector pHApr-1.

Vector p316 is generated in which the reshaped CD3 VH gene may be expressed in conjunction with different immunoglobulin H chain constant region genes, this vector being based on the pHâApr-gpt vector (Gunning et al., 1987, P.N.A.S. USA, 85, 7719-7723). A 1.65 Kb fragment of DNA carrying the dihydrofolate reductase (dhft) gene and SV 40 expression signals (Page & Sydenham, 1991, Biotechnology, 9, 64) is inserted into the unique EcoRI site of pHâApr-gpt. A 700 bp HindIII-BamHI DNA fragment encoding the reshaped CD3-VH gene is then cloned into the vector's multiple cloning site, downstream and under the control of the â actin promoter. The desired H chain constant region gene (in genomic configuration) can then be inserted into the unique BamHI restriction enzyme site downstream of the CD3-VH gene.

The aglycosyl human IgG1 constant region is derived from the wild type Glm (1, 17) gene described by Takahashi et al., (19S2, Cell, 29, 671-679) as follows. The gene is cloned into the vector M13 tg131 where site-directed mutagenesis is performed (Amersham International PLC kit) to mutate the amino acid residue at position 297 from an asparagine to an alanine residue.

Oligosaccharide at Asn-297 is a characteristic feature of all normal human IgG antibodies (Kabat et al., 1987, Sequence of Proteins of Immunological Interest, US Department of Health Human Services Publication), each of the two heavy chains in the IgG molecules having a single branched chain carbohydrate group which is linked to the amide group of the asparagine residue (Rademacher and Dwek, 1984, Prog. Immunol., 5, 95-112). Substitution of asparagine with alanine prevents the glycosylation of the antibody.

The 2.3 Kb aglycosyl IgG1 constant region is excised from M13 by double digestion using BamHI and BglII and ligated into the BamHI site of vector p316 to produce clone p323.

Subconfluent monolayers of dhfr⁻ Chinese Hamster Ovary cells are co-transfected with the vector p323 containing the heavy chain gene and a second vector p27$^4$ containing the re-shaped human ë light chain (Routledge et al., 1991, Eur. J. Immunol., 21, 2717-2725). Prior to tranfection both plasmid DNAs were linearised using the restriction endonuclease Pvul. Transfection is carried out using the DOTMA reagent (Boehringer, Germany) following the manufacturer's recommendations.

Heavy and light chain transfectants are selected for in xanthine/hypoxanthine free IMDM containing 5% (v/v) dialysed foetal calf serum.

The production of the analogous wild type human IgG1-CD3 heavy chain vector p278 has been described elsewhere (Routledge et al., 1991, Eur. J. Immunol., 21, 2717-2725 and GB9121126.8 incorporated herein by reference). H-chain expression vectors carrying the non-mutant human IgG2 (Flanagan & Rabbitts, 1982, Nature 300, 709-713), IgG3 (Huck et al., 1986, Nuc. Acid. Res., 14, 1779-1789), IgG4 (Flanagan & Rabbitts, 1982, Nature 300, 709-713), Epsilon (Flanagan & Rabbitts, 1982, EMBO. Journal 1, 655-660) and Alpha-2 (Flanagan & Rabbitts, 1982, Nature 300, 709-713) constant region genes (vectors p317, p318, p320, p321 and p325, respectively) are derived from the vector p316. Introduction of these vectors, in conjunction with the light chain vector p274, into dhfr⁻ CHO cells as described earlier, produced cell lines secreting CD3 antibody of the ã1, ã2, ã3, ã4, à and á-2 isotype respectively. Cells expressing CD3 antibodies were subjected to two rounds of cloning in soft agar, and then expanded into roller bottle cultures. The immunoglobulin from approximately 4 litres of tissue culture supernatant from each cell line is concentrated by ammonium sulphate precipitation, dialysed extensively against PBS and then quantified as follows:

As the antibody is not pure, a competition assay designed to specifically quantitate the concentration of antibody with CD3 antigen binding capacity was used. Human T-cell blasts are incubated with FITC labelled UCHT-1, an antibody which binds to the same epitope of the CD3 antigen as the chimeric panel. The concentration of FITC reagent used is previously determined to be half saturating. Unlabelled YTH 12.5 (HPLC purified) was titrated from a known starting concentration and added to wells containing T-cells and UCHT-1 FITC. The unlabelled antibody serves as a competitor for the antigen binding site. This is detected as decrease in the mean fluorescence seen when the cells are studied using FACS analysis. Thus, titration of the chimeric antibodies from unknown starting concentrations yields a series of sigmoidal curves when mean fluorescence is plotted against antibody dilution. These can be directly compared with the standard YTH 12.5 curve, an equivalent antibody may be used.

EXAMPLE 1

Preparation of an Aglycosylated Antibody Specific for the Human CD3 Antigen, Containing CDRs Corresponding in Sequence to Those from the YTH 12.5 Rat Antibody, in Human Heavy Chain Variable Framework Linked to IgG1 Constant Region and Rat Light Chain Variable Framework Linked to Human Lambda Constant Region.

A chain loss variant of YTH12.5LAG1 was selected for loss of CD3 light chain, that only expressing rat CD3 heavy chain, and was used for the purpose of transfecting in fully humanised aglycosyl CD3 heavy chain. A 1.4 kb BamHI-HindIII DNA fragment encoding the humanised IgG1 aglycosyl CD3 heavy chain construct was cloned into the multiple cloning site of two different expression vectors, pHβApr-1 gpt (Gunning et al (1987) P.N.A.S. USA 84, 4831 and 85, 7719-7723) and pOXCD52neo (Frewin unpublished) which contain different selectable markers.

pOXCD52neo expression vector is produced using the strong 'polypeptide chain elongation factor 1' promoter (EF1) which gives high-level antibody production (see Shigekazu Nagata NAR, Vol 18, No 17, page 5322. This is placed in a construct together with a neomycin selectable marker. Also included in the vector is a cDNA for Campath CD52 surface expressed antigen, driven by the TK promoter (all these promoters and markers are in the public domain by reason of availability). The expression of CD52 on the cell surface allows identification of transformants using CD52 antibodies.

YTH 12.5LAG1 was then transfected separately with the two plasmids by electroporation and heavy transfectants selected with IMDM containing 5% foetal calf serum, MPA and Xanthine for pHβApr-1gpt and IMDM containing 5% foetal calf serum and 1 mg/ml G418 for pOXCD52neo, over a couple of weeks until live colonies grew up for testing. Both transfections yielded positive clones when screened for human IgG1 production using ELISA. Functional CD3 antibody was tested for by binding to a human T cell line Jurkat (ATCC TIB 152 (J. Immunol 133, 123-128 (1984)) and analysed by FACS (Becton Dickinson), both assays showing yields of antibody of between 30 and 50 μg/ml.

The pOXCD52neo vector allows monitoring of transfected cells producing antibody with the use of a cell surface marker CD52. Only cells containing this marker secrete antibody so by taking Campath CD52 antibodies linked with FITC transfected cells can be analysed by FACS for the percentage of cells producing antibody and clonal status can be confirmed. No negative producing cells were detected and antibody yields remained at 50 μg/ml with normal cell growth.

A chimeric form of the aglycosyl CD3 antibody was produced using PCR assembly to link the rat CD3 light chain variable region to the human lambda constant region using primers which introduce restriction enzyme sites Hind III and EcoRI to allow cloning into the Celltech expression vector PEE12 (see Bebbington et al (1992) Biotechnology 10, 169). The primer sequences are SEQ ID No 29 and 30 in the sequence listing attached hereto.

The final construct was sequenced and cloned into PEE12 already containing the humanised CD3 aglycosyl heavy chain and this was transfected into the myeloma cell line NS0 (ECACC No 85110503-Galfre and Milstein (1981) Enzymology 73 (B) 3-46) by electroporation. Resultant clones were screened for antibody production using ELISA for human IgG1 and human lambda light chain and on the FACS for binding to human T-cell clone Jurkat cell line. The ELISA uses goat anti-human IgFc (Sigma 12136) as capture antibody and Biotinylated sheep anti-human IgG (Amersham RPN 1003) or Biotinylated goat anti-human lambda light chain (Amersham RPN 1188) as detector antibody. (see Routledge et al Eur. J. Immunol (1991) 21: 2717-2725).

After one transfection 16 clones expressed 60 μg/ml to 100 μg/ml, far more than any other transfection with the reshaped aglycosyl CD3. These transfectants were then cloned by limiting dilution cloning and some of these improved to 120 μg/ml. These remained stable in long term culture and large scale antibody production with no problems with cell growth.

FIGS. 1 to 4 illustrate the ability of these antibodies to bind CD3 with the same capacity as the previously described fully humanised aglycosyl anti-CD3 antibodies of the prior art.

The invention claimed is:

1. An IgG antibody having a binding affinity for the CD3 antigen complex comprising:
a heavy chain having the amino acid sequence SEQ ID NO:20;
a human lambda light chain constant region; and
a light chain variable domain comprising three CDRs having the amino acid sequences SEQ ID NOS:8, 10, and 12, and four framework regions having the amino acid sequences SEQ ID NOS: 35, 26, 27, and 28,
wherein alanine at amino acid 7 of SEQ ID NO:35 is replaced with proline.

2. An IgG antibody having a binding affinity for the CD3 antigen complex comprising:
a heavy chain having the amino acid sequence SEQ ID NO:20;
a human lambda light chain constant region; and
a light chain variable domain comprising three CDRs having the amino acid sequences SEQ ID NOS:8, 10, and 12, and four framework regions having the amino acid sequences SEQ ID NOS:25, 26, 27, and 28.

3. The antibody of claim 2, wherein the amino acid sequence of the light chain variable domain is SEQ ID NO:14.

4. The antibody of claim 3, wherein the amino acid sequence of the light chain is SEQ ID NO:18.

5. The antibody of claim 2, wherein the antibody is aglycosylated by replacing the amino acid corresponding to Asn 297 of the constant region heavy chain with an alternative amino acid residue.

6. The antibody of claim 5, wherein Asn 297 is replaced with an alanine.

7. The antibody of claim 2, in which the heavy chain constant region is of an IgG1 isotype.

8. The antibody of claim 1, wherein the antibody is monovalent.

9. The antibody of claim 2, wherein said antibody is in the form of a pharmaceutical composition comprising a physiologically acceptable diluent or carrier.

10. The antibody of claim 1, wherein the antibody is aglycosylated by replacing the amino acid corresponding to Asn 297 of the constant region heavy chain with an alternative amino acid residue.

11. The antibody of claim 10, wherein Asn 297 is replaced with an alanine.

12. The antibody of claim 1, in which the heavy chain constant region is of an IgG1 isotype.

13. The antibody of claim 2, wherein the antibody is monovalent.

14. The antibody of claim 1, wherein said antibody is in the form of a pharmaceutical composition comprising a physiologically acceptable diluent or carrier.

* * * * *

UNITED STATES PATENT AND TRADEMARK OFFICE
CERTIFICATE OF CORRECTION

PATENT NO.         : 7,994,289 B2
APPLICATION NO.    : 10/463442
DATED              : August 9, 2011
INVENTOR(S)        : Herman Waldmann and Mark Frewin It is certified that error appears in the above-identified patent and that said Letters Patent is hereby corrected as shown below:

Col. 1, line 37, "No.s" should read -- Nos. --.

Col. 3, line 59, "Van Lier" should read -- Van Ller --.

Col. 4, line 10, insert -- . -- after "by reference".

Col. 5, line 18, delete second closed ")" after "08/478,684".

Col. 7, lines 57-58, "genes may provided" should read -- genes may be provided --.

Col. 7, line 60, "known manner, g" should read -- known manner --.

Col. 9, line 23, "by way of is illustration" should read -- by way of illustration --.

Col. 10, line 60, "$V_L$" should read -- $V_L\lambda$ --.

Col. 11, line 3, "pHApr-1" should read -- pHβApr-1 --.

Col. 11, line 7, "pHâApr-gpt" should read -- pHβApr-gpt --.

Col. 11, line 11, "pHâApr-gpt" should read -- pHβApr-gpt --.

Col 11, line 21, "(19S2)" should read -- (1982) --.

Col. 11, line 41, "human ë light chain" should read -- human λ light chain --.

Col. 11, lines 64-65, "CD3 antibody of the ã1, ã2, ã3, ã4, å and á-2 isotype" should read -- CD3 antibody of the γ1, γ2, γ3, γ4, ε and α-2 isotype --.

Col. 14, line 5, "(Sigma 12136)" should read -- (Sigma I2136) --.

Signed and Sealed this
Thirty-first Day of July, 2012

David J. Kappos
*Director of the United States Patent and Trademark Office*